United States Patent [19]

Ishii et al.

[11] Patent Number: 4,838,698
[45] Date of Patent: Jun. 13, 1989

[54] EXTINCTION TYPE DETECTOR

[75] Inventors: Hiromitsu Ishii, Chiba; Takashi Ono, Yokohama, both of Japan

[73] Assignee: Hochiki Corp., Tokyo, Japan

[21] Appl. No.: 33,065

[22] Filed: Mar. 31, 1987

[30] Foreign Application Priority Data

Apr. 7, 1986 [JP] Japan .................................. 61-79434

[51] Int. Cl.[4] ............................................ G01N 21/59
[52] U.S. Cl. .................................. 356/437; 356/435; 356/223
[58] Field of Search ............... 356/433, 435, 437, 438, 356/439, 223; 340/630

[56] References Cited

U.S. PATENT DOCUMENTS

| 3,528,749 | 9/1970 | Bowker | 356/433 |
| 3,872,315 | 3/1975 | Boll | 356/439 |
| 3,992,113 | 11/1976 | Egli et al. | 356/435 |
| 4,119,949 | 10/1978 | Lindgren | 340/630 |
| 4,308,531 | 12/1981 | Yamamoto | 340/630 |
| 4,544,273 | 10/1985 | Berndt | 356/439 |
| 4,649,282 | 3/1987 | Ota et al. | 340/630 |

FOREIGN PATENT DOCUMENTS

2169401 7/1986 United Kingdom ................ 356/438

*Primary Examiner*—Richard A. Rosenberger
*Attorney, Agent, or Firm*—Lackenbach, Siegel, Marzullo & Aronson

[57] ABSTRACT

An extinct type detector which detects and determines a concentration or density of a gas or vapor in a space on the basis of an attenuation of light due to the gas or vapor present within the space.

The detector of this feature of the invention operates in such a way that the light emitting device is periodically driven to effect light emission, the first and the second photodetector devices receive the light from said light emitting device, the first and second storage means corresponding to the first and the second photodetector devices, respectively, cumulatively store the outputs from the respective photodetector devices, a difference in cumulative storage values between the first and the second storage means is detected to determine a concentration and density of the gas or vapor within the detecting space based on the detected difference.

11 Claims, 4 Drawing Sheets

EXTINCTION TYPE DETECTOR

BACKGROUND OF THE INVENTION

Field of the Invention and Related Arts

This invention relates to an extinction type detector for detecting a concentration or density of a gas or vapor within a space on the basis of an attenuation of light due to the gas or vapor present within the space.

In a conventional extinction type detector, a light emitting device and a photodetector device are disposed oppositely, keeping a space of 1m or so therebetween, so that a change in an amount of received light, which is causable by a gas or vapor intervening between the devices, such as a combustion gas, smoke, etc. caused, for example, by a fire.

However, such a conventional extinction type detector has a disadvantage that it requires a long detecting space as described above, rendering the detector bulky.

To solve this problem, there has been proposed a detector which utilizes reflecting mirrors for effecting multiple reflection so as to obtain a desired effect with a detecting distance reduced between the devices.

However, this proposed detector is complicated in structure and can not be small-sized as desired.

Further the devices commonly used as light emitting elements are, in general, liable to decrease their light emission due to deterioration with age or temperature fluctuation. If such a change in the performance is once caused, an output may be produced due to the deterioration of the elements even when gases or vapors of the same density or concentration come in. Thus, accurate detection can hardly be expected. More particularly, since the concentration or density is determined on the assumption that the value of the output is proportional to the concentration or density. Therefore, if the conditions of the light emitting element are changed and the light emission amount is reduced, decreasing the output value is lowered, the concentration or density of the gas or vapor entering is measured as if it is lowered.

OBJECT AND SUMMARY OF THE INVENTION

The present invention has been made with a view to obviating the problems involved in the conventional detectors and it is an object of the present invention to provide a detector provided with a compensation function which assures an output corresponding to the amount of the gas or vapor entering the detecting space without being influenced by possible fluctuation of the light emission amount, irrespective of possible fluctuation of light emission amount due to the deterioration of the light emitting element or temperature fluctuation.

It is another object of the present invention to provide an extinct type detector which is capable of obtaining a sufficiently large change in received light amount even when the detection length is curtailed, by accumulating photo-outputs obtained through intermittent light emission.

The present invention features an extinct type detector which detects and determines a concentration or density of a gas or vapor in a space on the basis of an attenuation o f light due to the gas or vapor present within the space.

The detector of the present invention comprises a power source; a light emitting device; a driven means for periodically driving the light emitting device for emitting light; a first photodetector device which is disposed at a position where it can receive light from said light emitting device and forms a gas or vapor detecting space between it and the light emitting device; a second photodetector device which is disposed at a position where it can receive light from said light emitting device and which receives said light under the conditions that the gas or vapor does not intervene between it and the light emitting device; a first storage means for cumulatively storing photo-outputs from said first photodetector device; a second storage means for cumulatively storing photo-outputs from said second photodetector device; and a determining means which detects a difference between the cumulative storage values of the first and the second storage means when said light emitting device stops its light emission and determines a concentration or density of said gas or vapor within the space on the basis of said difference detected.

The detector of this feature of the invention operates in such a way that the light emitting device is periodically driven to effect light emission, the first and the second photodetector devices receive the light from said light emitting device, the first and the second storage means corresponding to the first and the second photodetector devices, respectively, cumulatively store the outputs from the respective photodetector devices, a difference in cumulative storage values between the first and the second storage means is detected to determine a concentration and density of the gas or vapor within the detecting space based on the detected difference.

The present invention further features a detector comprising a power supply; a light emitting device; a drive means for periodically driving said light emitting device for effecting light emission; a first photodetector device which is disposed at a position where it can receive light from said light emitting device and forms a gas or vapor detecting space between it and the light emitting device; a second photodetector device which is disposed at a position where it can receive light from said light emitting device and which receives said light under the conditions that the gas or vapor does not intervene between it and the light emitting device; a first storage means for cumulatively storing photo-outputs from said first photodetector device; a second storage means for cumulatively storing photo-outputs from said second photodetector device; a suspending means for detecting the cumulative storage value of of said second storage means to suspend the driving of said light emitting device for light emission when said storage value reaches a predetermined value; and a determining means which determines the concentration or density of the gas or vapor within said detecting space based on a difference between the cumulative storage values of the first and the second storage means when said light emitting device stops its light emission.

The detector of this feature of the present invention operates in such a manner that the light emitting device is periodically driven to effect light emission, the first and the second photodetector devices receive the light from said light emitting device, the first and the second storage means corresponding to the first and the second photodetector devices, respectively, cumulatively store the outputs from the respective photodetector devices, the cumulative storage value of said second storage means is detected, the driving of said light emitting device for light emission is stopped when said storage value of said second storage means reaches the predetermined value, and the concentration or density of the gas or vapor within the detecting space is determined on the basis of a difference in cumulative storage values between the first and the second storage when said light emitting device stops the light emission.

The present invention further features a detector comprising a power supply; a light emitting device; a drive means for periodically driving said light emitting device for effecting light emission over a predetermined period of time; a first photodetector device which is disposed at a position where it can receive light from said light emitting device and forms a gas or vapor detecting space between it and the light emitting device; a second and a third photodetector device which are each disposed at a position where they can receive light from said light emitting device and which receive said light under the conditions that the gas or vapor does not intervene between it and the light emitting device; a first storage means for cumulatively storing photo-outputs from said first photodetector device; a second storage means for cumulatively storing photo-outputs from said second photodetector device; a light emission control means for varying the amount of light emission of the light emitting device on the basis of a photo-output from said third photodetector device so that the photo-outputs from said second and said third photodetector device may substantially be equal to each other; a determining means which determines the concentration or density of the gas or vapor within said detecting space based on a difference between the cumulative storage values of the first and the second storage means when said light emitting device stops its light emission.

With this feature, the detector of the present invention operates in such a manner that the light emitting device is periodically driven to effect light emission, the first photodetector device and the second and third photodetector devices receive the light from said light emitting device, the first and the second storage means corresponding to the first and the second photodetector devices, respectively, cumulatively store the outputs from the respective photodetector devices, the light emission amount of said light emitting device is varied, on the basis of the photoouputs from the second storage means and the third photodetector device, so that the photo-outputs from the second and the third photodetector devices may substantially be equal to each other, and the concentration or density of the gas or vapor within the detecting space is determined on the basis of a difference in cumulative storage values between the first and the second storage when said light emitting device stops the light emission after said predetermined period of time.

DESCRIPTION OF PREFERRED EMBODIMENTS OF THE INVENTION

Preferred embodiments of the present invention will now be described. The following exemplarily referrs to a smoked detector for detecting smoke due to a fire etc., but the present invention is by no means limited thereto.

Figure 1:
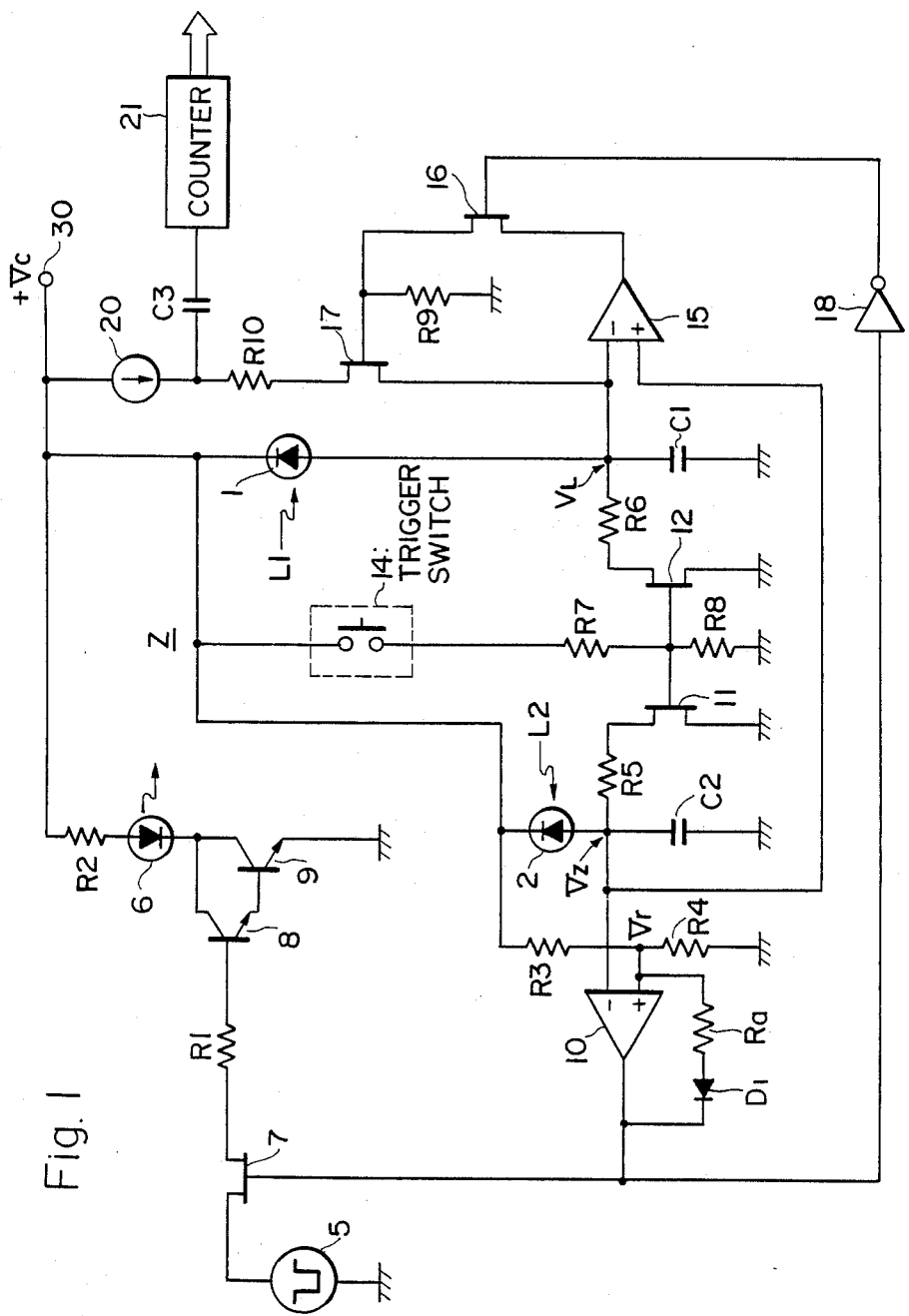
FIG. 1 is a block diagram of a first embodiment of the present invention.

FIG.1 is a circuit diagram showing an embodiment of the present invention.

The formation will first be described. 5 is a pulsive oscillation source, which outputs an oscillation pulse having a predetermined frequency to intermittently drive the light emitting device 6 for effecting light emission. The oscillation pulse from the pulsive oscillation source 5 is supplied to a light emission drive circuit formed of transistors 8 and 9, which are Darlington-connected through an analog switch 7 comprising FET, through a resistor R1. The collector of the transistor 9 forming the light emission drive circuit is connected to the light emitting device 6 and a load resistor R2 in series with the latter. In the figure, 30 is a power source having a voltage of $+Vc$ volt.

A photodetector device 1 for smoke detection is disposed at a position opposite to the light emitting device 6 to form a smoke detecting space z. The distance between the light emitting device 6 and the photodetector device 1 may be as short as 5 cm. The smoke detecting space z is so formed that external smoke may freely enter. Therefore, the photodetector device 1 detects light (hereinafter referred to as "detected light L1") through the smoke detecting space z. A photodetector device 2 for reference is so disposed that it can receive light (hereinafter referred to as "reference light L2") emitted from the light emitting device 6 without passing through the smoke detecting space z. For example, an optical fiber may be provided between the devices 2 and 6 so that the light receiving amount may substantially be equal to a light emission amount.

A first capacitor C1 is connected in series to the photodetector device 1 for smoke detection, while a second capacitor C2 is connected in series to the photodetector device 2 for reference so that the photo-outputs from the photodetector devices 1 and 2 are charged cumulatively. These capacitors C1 and C2 function as storage means, respectively, as will be described in detail later. The capacitors C1 and C2 have substantially the same performances.

At this time, if smoke is not present within the smoke detecting space, the detection light L1 and the reference light L2 irradiate the photodetectors 1 and 2 with the same intensity. Thus, if smoke is not within the smoke detecting space, the charged amounts in the capacitors C1 and C2 are equal and terminal voltages E1 and E2 are also equal to each other. If smoke enters the smoke detecting space, the light amount of the detected light L1 received by the photodetector device 1 is reduced in proportion to the density or concentration of the entering smoke. As a result of this, there is caused a difference in charged amounts between the capacitors C1 and C2 and accordingly caused a difference between the terminal voltages V2 and V1.

A charge voltage V2 of the capacitor C2 connected in series with the photodetector device 2 for reference is input to a ($-$) side of a comparator 10, while a reference voltage Vr determined by a divided voltage between resistors R3 and R4 is set at a (+) side input of the comparator 10.

The comparator 10 generates a H-level output to render the analog switch 7 comprising FET conducting when the charge voltage V2 of the capacitor C2 is smaller than the reference voltage Vr. When the charge voltage V2 of the capacitor C2 reaches the reference voltage Vr, the output from the comparator will be inverted to L-level to turn off the analog switch 7. Thus, the comparator 10 and the analog switch 7 constitute a light emission stopping circuit for the light emitting device 6.

Further the (+) side input and the output of the comparator 10 is connected through a feedback resistor Ra and a diode D1. By virtue of such the connection, the comparator 10 is set to have an appropriate hysteresis, and also to prevent a leak current which may flow into the analog switch 7 and into a inverter which will mentioned in the following description.

Another analog switch for resetting is connected in parallel with the capacitor C2 through a resistor R5. Similarly, a further analog switch 12 for discharge resetting is provided in parallel with the capacitor C through a resistor R6. The analog switches 11 and 12 are rendered conducting upon receipt of a gate bias determined by a divided voltage between resistors R7 and R8 when a trigger switch 14 is closed. As a result of this, the capacitors C1 and C2 begin discharging to reset the charging state as described above.

On the other hand, the charged voltage V2 of the capacitor C2 and the charged voltage V1 of the capacitor C1 are input to a comparator 15. The comparator 15 receives, at its (−) input, the charged voltage V1 of the capacitor C1 and, at its (+) input, the charged voltage V2 of the capacitor C2. Therefore, when no smoke enters the smoke detecting space, the charged voltages of the capacitors C1 and C2 are equal to each other and an output from the comparator 15 is at a low level. If smoke enters the smoke detecting space, there is caused a difference between the charged voltages V1 and V2 of the capacitors C1 and C2 and there is formed a relation V2>V1. As a result of this, the output from the comparator will be H-level.

The output from the comparator 15 is supplied to a gate of an analog switch 17 through an analog switch 16. An output from the comparator 10 is supplied, after being inverted by an inverter 18, to a gate of FET constituting the analog switch 16. Until the charged voltage V2 of the capacitor C2 based on the reference light L1 reaches the reference voltage Vr, the output from the comparator 10 is at a H-level and, therefore, the analog switch 16 is in it off-state in response to the L-level output inverted by the inverter 18. When the charged voltage V2 of the capacitor C2 reaches the reference voltage Vr and the output from the comparator 10 is inverted to L-level, then the analog switch 16 will be conductive in response to the H-level output inverted by the inverter 18.

The analog switch 17 receives, at its gate, an output from the comparator 15 through the analog switch 16. The analog switch 17 is so connected that a pulse current source 20 may be connected to the first capacitor C1 through a resistor 10 for supplying a charging current. A pulse output from the pulse current source 20 is input to a counter 21 through a capacitor C3 for cutting off a DC current.

A circuit portion formed of the comparator 15, the analog switches 16 and 17, the inverter 18, the pulsive current source 20 and the counter 21 function as a circuit for detecting a concentration or density of smoke on the basis of a difference (ΔV) in charged voltages between the capacitors C1 and C2 when the light emitting device 6 stops its light emission in response to the L-level output from the comparator 10.

In this connection, it is to be noted that the trigger switch 14 is once closed to start the operation of the circuit and after the operation has been started, it is repeatedly closed for a while, at a timing that the counting operation of the counter 21 is stopped, by a timing control circuit not shown.

The operation of the embodiment as illustrated in FIG. 1 will be described.

First, the trigger switch 14 is closed to render the analog switches 11 and 12 conducting by the gate bias determined by the divided voltage between the resistors R7 and R8. As a result of this, the capacitors C1 and C2 start discharging and reset the charging states. Thereafter, the trigger switch 14 is opened. Since the output from the comparator 10 is at a H-level (V2<Vr), the analog switch 7 becomes conducting so that oscillation pulse from the pulsive oscillation source 5 is supplied to the light emission drive circuit formed of the transistors 8 and 9. Thus, the light emitting device 6 is intermittently driven, in response to the oscillation pulse from the pulsive oscillation source 5, to effect intermittent light emission. The light emitted by the intermittent light emission by the light emitting device 6 is incident upon the photodetector device 1 for smoke detection as the detection light L1 through the smoke detecting space Z into which smoke is allowed to enter. This emitted light is simultaneously incident upon the photodetector device 2 as the reference light L2 without passing through the smoke detecting space Z. As a result of this, a photo-current is allowed to flow through the photodetector device 2, upon which the reference light L2 is incident, to charge the capacitor C2. At the same time, a photo-current is allowed to flow through the photodetector device 1, upon which the detection light L1 is incident, to charge the capacitor C1 over a light receiving period of time. Thus, the capcitors C1 and C2 is charged, upon every driving of the light emitting device 6, according to the respective photo-currents, to cumulatively store the photocurrents therein, respectively.

After repetition of these intermittent light emissions, the charged voltage V2 cumulatively stored in the capacitor C2 is raised to reach the reference voltage Vr of the comparator 10 after a time period T1 has been passed. Then, the output of the comparator 10 is inverted from a H-level to a L-level. This output inversion renders the analog switch 7 nonconducting to stop the light emission driving of the light emitting device 6. Upon this stopping of the light emission driving, the capacitors C1 and C2 hold their respective charged voltages V1 and V2 at the time of the stopping of the light emission.

On the other hand, the L-level output of the comparator 10 is inverted by the inverter 18 to render the analog switch 16 conducting.

At this time, if no smoke is present within the smoke detecting space, the detection light L1 and the reference light L2 are received, in the same light amounts, by the respectively corresponding photodetector devices 1 and 2. The charged voltages V1 and V2 indicative of the cumulative charged amounts of the capacitors C1 and C2, respectively, are equal to each other. Since the comparator 15 is set to turn down its output to low level when the charged voltages V1 and V2 are equal to each other, the trigger switch 14 is closed after a predetermined time has passed and the capacitors C1 and C2 begin to discharge and are thus reset.

If smoke is present within the smoke detecting space Z, the detection light L1 is attenuated by the smoke and the charged voltage V1 of the capacitor C1 is lower than the charged voltage V2 of the capacitor C2. As a result of this, the comparator 15 generates an output of H-level. This H-level output renders the analog switch 16 conducting so that the analog switch 17 is rendered conducting in response to the H-level output from the comparator 15. The pulse current source 20 is connected in series to the first capacitor C1 through the resistor R10 and the analog switch 17.

Immediately after the light emission has been stopped, a pulse current from the pulse current source 20 is supplied only to the capacitor C1. While the charged voltage V2 of the capacitor C2 is held at a level when the light emission is stopped, only the capacitor C1 begins to be charged by the pulse current to raise its charged voltage V1. The pulse current for charging the capacitor C1 to raise its charge voltage is also supplied to the counter 21 through the capacitor C3 simultaneously, to count the number of pulses. When the charged voltage V1 of the capacitor C1 by the cumulative charging of the pulse current becomes equal to the charged voltage V2 held in the capacitor C2 at a time T2, the output of the comparator 15 is inverted to a L-level. This turns the analog switch 17 off and the capcitor C1 is disconnected from the pulse current source 20. The then count number of the counter 21 is proportional to a difference ($\Delta V$) in charged voltages between the capacitors C2 and C1 when the light emission is stopped. From this counter number by the counter 21, a concentration or density of smoke or extinction (%/m) is calculated.

Furthermore, upon inversion of the output from the comparator 16 to L-level, a timing control circuit not shown temporally turns on the trigger switch 14 to effect discharging of the capacitors C1 and C2 for resetting so as to start a next detection cycle.

A time-chart of FIG. 2 is now referred to, for explaining a compensation operation when the light emission amount of the light emitting device is lowered.

Figure 2A:
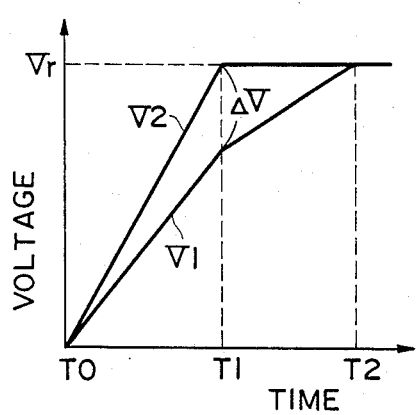
FIGS. 2(a) and (b) are diagrams each showing the charging state of a capacitor shown in FIG. 1.
Figure 2B:
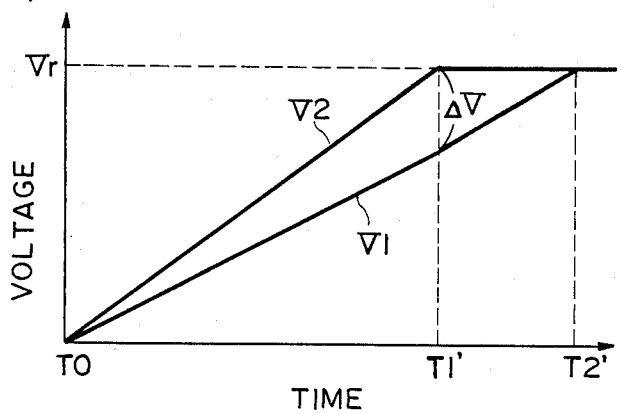
Figure 3:
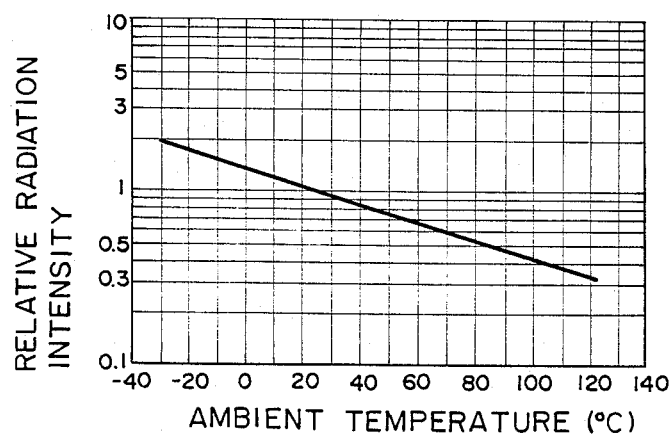
FIG. 3 is a diagram showing an influence of an ambient temperature upon a light emitting element.

When the light emitting device 6 is driven to emit light under the conditions that smoke is introduced, at some given density, into the smoke detecting space, the charged voltage of the capacitors C1 and C2 rise substantially linearly. At this time, if there is no change in light emission amount of the light emitting device 6 due to the deterioration of the materials of the device or due to the possible fluctuation in ambient temperature, the charged voltage varies as illustrated in FIG. 2(a). Whereas, if there is such a change in light emission amount of the light emitting device, the charged voltage varies as illustrated in FIG. 2(b). For example, if an infrared LED (GaAlAs infrared light emitting device) is used as the light emitting device 6, there is caused a change in intensity of emitted infrared light accompanying an ambient temperature fluctuation as shown in FIG. 3.

It is now assumed that the light emission amount of the light emitting device 6 is lowered due to the deterioration of the light emitting device 6 or the fluctuation of ambient temperature and the detection light L1 is reduced to L1a and the reference light L2 is reduced to L2a, the photo-outputs obtainable by one light emitting driving of the light emitting device 6 for charging the capacitors C1 and C2 are reduced according to the lowering of the light emission amount. The light emitting driving of the light emitting device 6 is repeated until the charged voltage V2 of the capacitor C2 reaches the reference voltage Vr of the comparator 10 at a time T1'. The time T1' is longer than a time T1 which is set for the original conditions under which no lowering of the light emission amount is not caused. When the charged voltage V2 reaches the reference voltage Vr, the light emission is stopped. In this case, the slope of the line indicative of the relationship between the light emitting time and the charged voltage is more gentle as shown in FIG. 2(b). The time (T1') for the charged voltage V2 of the capacitor C2 to reach the reference voltage Vr is prolonged due to the reduction of the the light emission amount as compared with the time T1 for the original conditions. The total amount of received lights within the time T1 under the original conditions and within the time T1' under the particular conditions as referred to above are the same.

By the reason as described above, even if the light emission amount of the light emitting device is reduced, the charged voltages V1 and V2 held in the capacitors C1 and C2 when the driving of the light emission is stopped as a result of the reaching of the charged voltage V2 of the capacitor C2 to the reference voltage are not changed irrespective of the change in light emission amount. Thus, the extinction due to the smoke is influenced only by the density or concentration of the smoke, even if the light emission amount is lowered. Therefore, if the capacitor C2 is continued to be charged until the charged voltage V2 of the capacitor C2 reaches the reference voltage Vr under the conditions where smoke is present within the smoke detecting space Z, the charged voltage of the capacitor C1 is equal to the voltage V1 under the conditions where the light emission amount is not lowered. Thus, the difference $\Delta V$ in voltages is the same despite of the change in light emission amount. The charging time T2—T1, T2$\alpha$—T1' for the difference $\Delta V$ in voltages for the capacitor C1 is constant.

In this connection, it is to be noted that photooutputs for the capacitors C1 and C2 may possibly contain noise signals due to external disturbing light. However, a positive and a negative component are cancelled in the charging by the capacitors C1 and C2. Therefore, a possible influence by the noises can be neglected.

Although the comparator 15 is employed as a comparing means in the present embodiment as illustrated, it may be replaced by a differential amplifier circuit. In this case, a difference ($\Delta V$) in voltage between the capacitors C1 and C2 is detected as a detection signal of smoke amount in the form of an analog amount.

Figure 4:
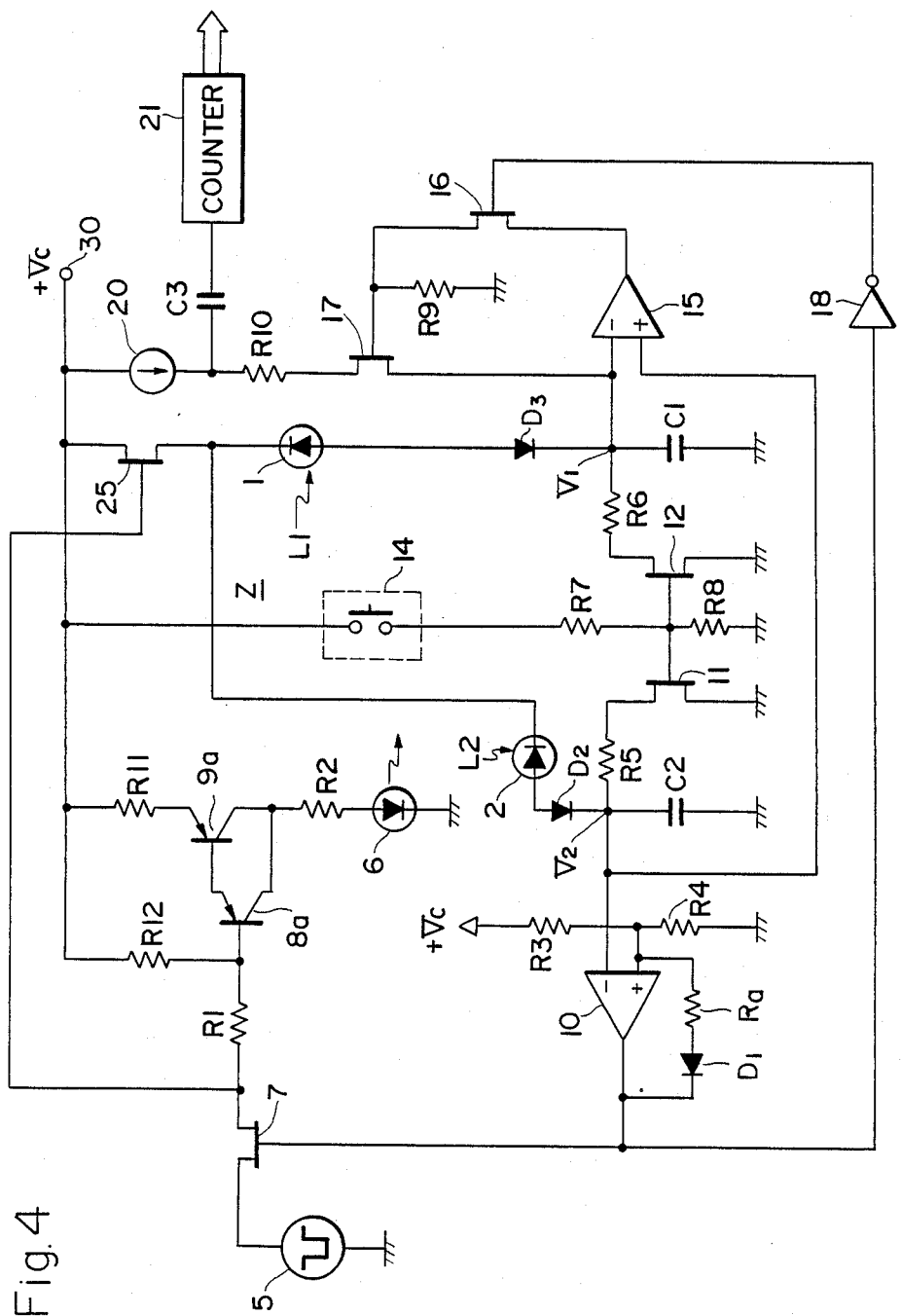
FIG. 4 is a block diagram of a second embodiment of the present invention.

FIG. 4 is a circuit diagram illustrating another embodiment of the present invention. In this embodiment, possible errors in the charged voltage of the capacitors due to a leak current from the photodetector device are eliminated.

The photodetector device 1 for smoke detection and the photodetector device 2 for reference may allow currents of triffle amounts to leak therefrom, depending upon the kinds of the devices, for example photodiodes, even under the conditions where no light from the light emitting device is incident thereupon. These leak currents may possibly prevent accurated cumulative charging of the photo-outputs. to obviate this problem, an analog switch 25 comprising FET is inserted in a common power supply line for applying a power voltage +Vc to the photodetector device 1 for smoke detection and the photodetector device 2 for reference. A characteristic of the analog switch 25 is reverse of that of the analog switch 7. The output of the analog switch 7 is flow into a gate of the analog switch 25. An oscillation pulse from the pulse oscillator 5 is supplied to a gate of an analog switch of FET 25. The analog switch 25 is turned on only at the timing of the driving for light emission and it is kept off during the time when the light emission is not effected, to prevent the leak currents from the photodetector devices 1 and 2 from being charged in the capacitors C1 and C2.

The remaining formation of this embodiment is substantially identical with that of the first embodiment as illustrated in FIG. 1 except that the light emission driving circuit is formed of PNP transistors 8a and 9a.

Figure 5:
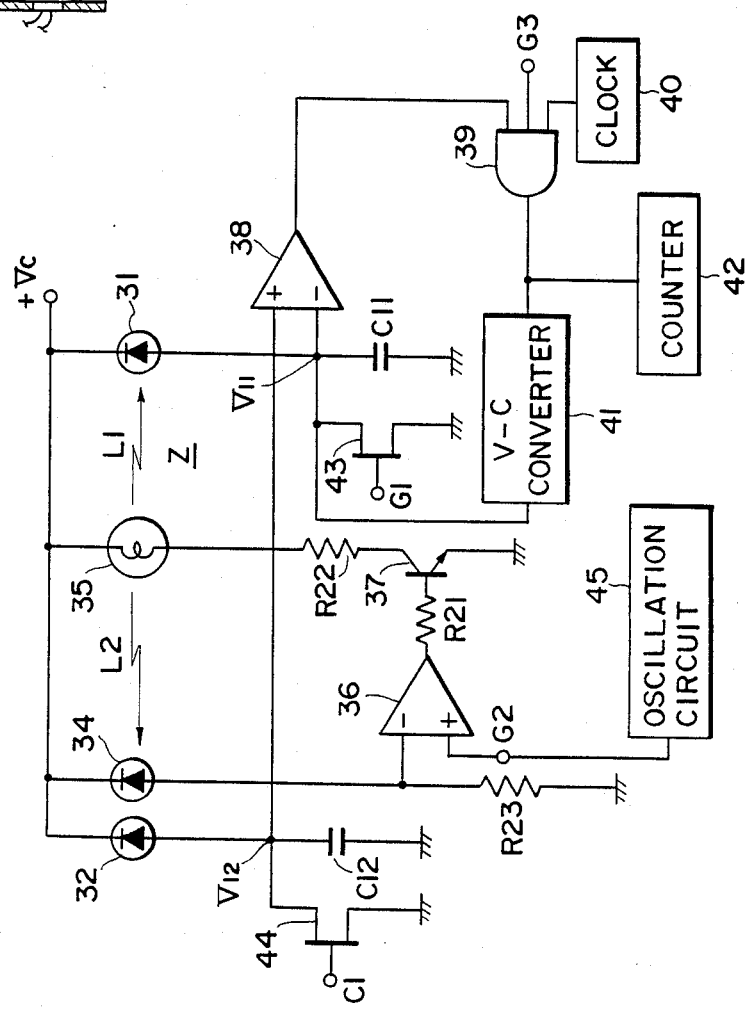
FIG. 5 is a block diagram of a third embodiment of the present invention.

FIG. 5 illustrates a further embodiment of the present invention. In this embodiment, another photodetector device for temperature compensation, which receive the light from the light emitting device 6 without passing through the smoke detecting space as the photodetector device 2 for reference is further provided.

The formation of this embodiment will first be described. 35 is a light emitting device which comprises a lamp in this embodiment as illustrated. A light emission driving circuit comprising an operational amplifier 36 and a transistor 37 is provided as a light emission driving means.

A predetermined number of light emission driving pulses are supplied, every detection period, to a (+) input of the operational amplifier 36 from an oscillation circuit 45 connected to a terminal G2. As an oscillation pulse from the oscillation circuit 45, for example a train of 10 light emission driving pulses is employed. This can be attained by inputting the oscillation output to one input of an AND gate and holding the other input of the AND gate at H-level only during a time while 10 light emission driving outputs are output.

The output of the operational amplifier 36 is connected to a base of the transistor 37. A collector of the transistor is connected to the light emitting device 35 through a current limiting resistor R22.

Although a lamp is used as the light emitting device in the embodiment as illustrated, a light emitting diode may be employed instead.

The arrangement of the light emitting device 35 and a photodetector device 31 for smoke detection is similar to those in the embodiment as illustrated in FIG. 1.

In FIG. 5, 34 is a photodetector device for temperature compensation. This photodetector device 34 and a photodetector 32 for reference are disposed so as to receive the reference light L2 from the light emitting device 35 without passing through the smoke detecting space Z. As in the foregoing embodiments, the photodetector devices 32 and 34 may be connected to the light emitting device 35 through optical fibers.

The photodetector device 34 for temperature compensation is connected in series to a resistor R23 and the juncture between the photodetector 34 and the resistor R23 is connected to an input terminal of a (−) terminal of the operational amplifier 36 which constitutes the light emission driving circuit. The photodetector device 34 for temperature compensation adapted to receive the reference light L1 and a gain control circuit of the operational amplifier 36 comprising the resistor 23 constitutes a temperature compensation means.

A capacitor C12 as a first storage means is connected in series with the photodetector device 32 for reference which receives the reference light L2 from the light emitting device 35. A capacitor C11 as a second storage means is connected in series to the photodetector device 31 for smoke detection which receives the smoke detection light L1 from the light emitting device through the smoke detecting space Z.

The capacitors C12 and C11 are adapted to cumulatively store photo-outputs based on the detection light L2 and the reference light L1 received through a predetermined number of times of light emission driving of the light emitting device 35.

The charged voltage of the capacitor C12 is applied to a (+) input terminal of a comparator 38. The charged voltage of the capacitor C11 is applied to a (−) input terminal of the comparator 38. If the charged voltage of the capacitor C12 is assumed as V12 and the charged voltage of the capacitor C11 is assumed as V11, the comparator 38 produces a H-level output when V12>V11.

An output from the comparator 38 is applied to a three terminal AND gate 39. One of the remaining two inputs of the AND gate is connected to an output of a clock oscillator 40. The rest of the input terminals of the AND gate is taken out as a terminal G3. The terminal G3 becomes H-level at the timing when the predetermined number of light emission driving of the light emitting device 5 has been completed to render the AND gate 39 enable. More specifically, upon termination of the supply of the predetermined number of light emission driving pulses to the terminal G2 of the operational amplifier 36, the terminal G of the AND gate 39 is thrown into H-level over a predetermined smoke detecting period.

An output from the AND gate 39 is supplied to a voltage-current converter (hereinafter referred to as "V-C converter") 41. This V-C converter 41 converts the clock pulse output from the clock oscillator 40 into a current pulse. An output from the V-C converter 41 is connected to the capacitor C11. By this reason, the capacitor C11 is charged also with the current pulse from the V-C converter 41. An output from the AND gate 39 is further supplied to a counter 42. The counter 42 counts the clock pulses from the AND gate 39.

Analog switches each comprising FET are connected in parallel with the capacitors C11 and C12, respectively. When a driving pulse is supplied to the terminal G1 every detecting period, the analog switches 43 and 44 are turned on to discharge the capacitors C11 and C12, respectively, for resetting them.

The operation of the embodiment as illustrated in FIG. 5 will now be described.

When no smoke enters the smoke detecting space Z, the light amounts of the reference light L2 and the smoke detection light L1 resulting from the light emission driving of the light emitting device 35 are equal to each other. The charged voltages V11 and V12 of the capacitors C11 and C12 which cumulatively store the photo-outputs from the photodetector device 31 for smoke detection and the photodetector device 32 for reference are also equal to each other. Therefore, when the predetermined number of light emission driving has been completed, the output from the comparator 38 is at a L-level and the AND gate 39 is in an inhibited state. As a result of this, the charging of the capacitor C11 by the clock pulses is not effected. The count number of the counter 42 is zero and it is determined that no smoke enters the smoke detecting space Z.

If smoke enters the smoke detecting space Z, the smoke detection light L1 obtained through the predetermined number of intermittent light emission driving operations of the light emitting device 35 is attenuated according to the density or concentration of the smoke. The charged voltage V12 of the capacitor C12 is increased linearly with a certain slope over a light emission period T1, according to the increase of the number of light emission, as the voltage 12 is not influenced by the entering of smoke into the smoke detecting space Z. While the charged voltage V11 of the capacitor C11 is attenuated according to the amount of the entering smoke. Thus, the charged voltage V11 is lower, in the increase rate, than the charged voltage V12 of the capacitor C12. As a result, there is caused a difference $\Delta V$ in charged voltages at the time T1 when the light emission driving is stopped.

Because of this difference $\Delta V$ in charged voltages, the output from the comparator 38 becomes H-level at the time T1 when the light emission driving of the light emitting device 35 is stopped. At this time, if the terminal G3 is rendered H-level, then the AND gate 39 is put into an enable state, to supply the clock pulses from the clock oscillattion circuit 40 to the V-C converter 41. As a result of this, current pulses corresponding to the clock pulses are supplied to the capacitor C11 to start charging of the capacitor C11 by the clock pulses from the time T1.

When the charged voltage V11 of the capacitor C11 by the clock pulses reaches the charged voltage V12 of the capacitor C12, i.e. the reference voltage Vr, at the time T2, the output from the comparator 38 is lowered to a L-level to put the AND gate 39 into an inhibiting state. Thus, the charging of the capacitor C11 by the clock pulses is stopped.

In these operations, the clock pulses output from the AND gate 39 over the time from T1 to T2 are counted by the counter 42, and the counter number of the counter 42 when the output of the clock pulses is stopped at the time T2 corresponds to an amount of the smoke entering the smoke detecting space Z. Thus, the smoke density or concentration and the extinction (%/m) are calculated from the count number of the counter 42.

When the predetermined detection period is terminated after completion of the calculation of the extinction etc. based on the count number of the counter 42, a resetting pulse is supplied to the terminal G1 of the analog switches 43 and 44 to discharge the capacitors C11 and C12 for resetting them. Thereafter, a similar smoke detection processing is repeated, upon supplying of the light emission driving pulse to the terminal G2.

On the other hand, of the light emission amount of the light emitting device 35 is changed due to, for example, a fluctuation in ambient temperature, a gain control is carried out for the operational amplifier 36, on the basis of the fluctuation in the photo-output of the photodetector device 34 for temperature compensation. More specifically, if the ambient temperature fluctuates, the inserted output from the operational amplifier 36 becomes larger and, by effecting a gain control for this, the light emission from the light emitting device 35 is kept constant, based on the photo-output from the photodetector device 34 for temperature compensation, relative to the other photodetector devices, irrespective of possible ambient temperature fluctuation. Thus, the light output is kept unvaried in relation with the photodetectors, despite of possible fluctuation of ambient temperature, assuring accurated measurement of the smoke density or concentration.

Moreover, the light emitting time is set constant in the present embodiment, so that a influence by a leak current to be charged to the capacitors C11 and C12 through the photodetector devices 31 and 32 can be limited in a certain scope. Therefore, even if the light emission amount is lowered, the influences of the leak currents upon the density measurement can advantageously be neglected.

However, please note that a resetting pulse may be supplied to the terminal G1 at the timing when the output from the comparator 38 is lowered from H-level to L-level and the charging of the capacitor C11 by the clock pulses is stopped, to start a further light emission driving operation. In this case, the smoke density or concentration and the extinction are calculated during the succeeding period of light emission driving, based on the count number of the counter 42 obtained in the previous period.

Although the photo-outputs of the reference light and the smoke detection light are cumulatively charged in the capacitors in the foregoing embodiments, the photo-outputs may be converted into digital signals and cumulatively stored in memories. In this case, the calculating processing of the smoke amounts based on the cumulatively stored photo data is also carried out in the digital form to obtain a smoke density or concentration and an extinction according to a difference between the signals at the time when the light emission is stopped.

Furthermore, the light emitting device is intermittently driven for effecting the predetermined number of light emissions for every detection period in the foregoing embodiments, but the light emission may be carried out not intermittently but continuously. In this case, the photoouptputs are likewise added cumulatively.

Although all the embodiments as given above refers to the detector for smoke detection, the present invention can of course be applied to the detection of density or concentration of another gas or vapor. For example, for the detection of a gas, laser light may be used as a light source and a photodetector device for detecting the spectrum of absorption by the gas may be employed.

Figure 6:
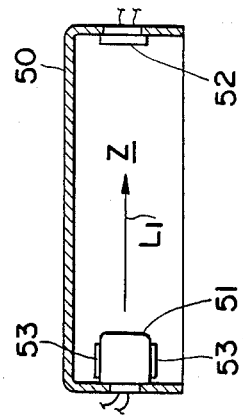
FIG. 6 is a fragmentary sectional view of a detector, showing an example of the arrangement of a light emitting device and a photodetector device.

Furthermore, the light emitting device may be covered by an outer tube and the outer or inner surface of this outer tube may be attached with a photodetector device such as a photocell. In this case, the detector may advantageously be structured in an extremely compact form. The arrangement of this detector is as illustrated in FIG. 6. In FIG. 6, 50 is a base, 51 is the outer tube containing the light emitting device therein, 52 is a photodetector for detection, and 53 is a photocell which may be used for reference or temperature compensation. The spacing between the outer tube 51 and the photodetector device 52 for detection may be reduced to 5cm or so. The arrangement of FIG. 6 may also adopted when a lamp is used as the light emitting device.

And the means comprising the circuits of FIG. 1 or FIG. 4 and of FIG. 5 can be combined in one circuit to obtain the desired object of the invention.

We claim:

1. An extinction type detector which detects and determines a concentration or density of a gas or vapor in a space on the basis of an attenuation of light due to the gas or vapor present within the space, which detector comprises:

a light emitting device;

drive means for periodically and repeatedly driving the light emitting device for emitting light in a sequence of ON/OFF cycles;

a first photodetector device which is disposed at a position where it can receive light from said light emitting device, a gas or vapor detecting space existing between said first photodetector device and said light emitting device;

a second photodetector device which is disposed at a position where it can receive light from said light emitting device, said light being received under the conditions that the gas or vapor does not intervene between said second photodetector device and said light emitting device;

first storage means for cumulatively storing photooutputs from said first photodetector device;

second storage means for cumulatively storing photo-outputs from said second photodetector device, said stored outputs being accumulated as storage values from a plurality of said ON/OFF cycles of said light emitting device, the storage value in each said storage means increasing for each cycle wherein the associated photodetector device receives light, and means for limiting the number of said cycles in said sequence of ON/OFF cycles, determining means which, after said sequence of ON/OFF cycles is complete, detects a difference between the cumulative storage values of the first and the second storage means and determines a concentration or density of said gas or vapor within the space on the basis of said detected difference in cumulative values, said storage values representing said cumulative stored plurality of photo-outputs.

2. An extinction type detector as claimed in claim 1, in which said storage means are capacitors having characteristics substantially the same as each other and said determining means includes a comparing means which compares the charged amounts between the capacitors to determine the difference.

3. An extinction type detector which detects and determines a concentration or density of a gas or vapor in a space on the basis of an attenuation of light due to the gas or vapor present within the space, which detector comprises:

a light emitting device;

drive means for periodically driving the light emitting device for emitting light in a sequence of ON/OFF cycles;

a first photodetector device which is disposed at a position where it can receive light from said light emitting device, a gas or vapor detecting space existing between said first photodetector device and said light emitting device;

a second photodetector device which is disposed at a position where it can receive light from said light emitting device, said light being received under the conditions that the gas or vapor does not intervene between said second photodetector device and said light emitting device;

first storage means for cumulatively storing photooutputs from said first photodetector device;

second storage means for cumulatively storing photo-outputs from said second photodetector device, said stored outputs being accumulated from a plurality of said ON/OFF cycles of said light emitting device; and determining means which detects a difference between the cumulative storage values of the first and the second storage means and determines a concentration or density of said gas or vapor within the space on the basis of said detected difference in cumulative values, said storage values representing said cumulative stored plurality of photo-outputs;

said storage means being capacitors having characteristics substantially the same as each other and said determining means including a comparing means which compares the charged amounts between the capacitors to determine the difference.

said determining means further including charging means for charging at a controlled rate the first capacitor with a charge in proportion to the difference between the cumulative storage values detected by said comparing means, and counting means for indicating said charge input of said charging means, to determine the density or concentration of said gas or vapor on the basis of the indicated charge input.

4. An extinction type detector which detects and determines a concentration or density of a gas or vapor in a space on the basis of an attenuation of light due to the gas or vapor present within the space, which detector comprises:

a light emitting device;

drive means for periodically and repeatedly driving said light emitting device for effecting light emission in a sequence of ON/OFF cycles;

a first photodetecting device which is disposed at a position where it can receive light from said light emitting device, a gas or vapor detecting space existing between said first photodetector device and said light emitting device;

a second photodetector device which is disposed at a position where it can receive light from said light emitting device, said light being received under the conditions that the gas or vapor does not intervene between said second photodetector device and said light emitting device;

first storage means for cumulatively storing photooutputs outputs from said first photodetector device; second storage means for cumulatively storing photo-outputs from said second photodetector device, said stored outputs being accumulated as storage values from a plurality of said ON/OFF cycles of said light emitting device, the storage value in each said storage means increasing for each said cycle wherein the associated photodetector device receives light, suspending means for detecting the cumulative storage value of said second storage means and for suspending the driving of said light emitting device for light emission when said storage value reaches a predetermined value; and determining means which determines the concentration or density of the gas or vapor within said detecting space based on a difference between the cumulative storage values of the first and the second storage means when said light emitting device stops its light emission.

5. An extinction type detector as claimed in claim 4, in which said storage means are capacitors having characteristics substantially the same as each other and determining means includes a comparing means which after said cumulative storage is suspended compares the charged amounts between the capacitors to determine the difference.

6. An extinction type detector which detects and determines a concentration or density of a gas or vapor in a space on the basis of an attenuation of light due to the gas or vapor present within the space, which detector comprises:

a light emitting device;

drive means for periodically driving said light emitting device for effecting light emission in a sequence of ON/OFF cycles;

a first photodetecting device which is disposed at a position where it can receive light from said light emitting device, a gas or vapor detecting space existing between said first photodetector device and said light emitting device;

a second photodetector device which is disposed at a position where it can receive light from said light emitting device, said light being received under the conditions that the gas or vapor does not intervene between said second photodetector device and said light emitting device;

first storage means for cumulatively storing photooutputs from said first photodetector device; second storage means for cumulatively storing photo-outputs from said second photodetector device, said stored outputs being accumulated from a plurality of said ON/OFF cycles of said light emitting device;

suspending means for detecting the cumulative storage value of said second storage means and for suspending the driving of said light emitting device for light emission when said storage value reaches a predetermined value; and determining means which determines the concentration or density of the gas or vapor within said detecting space based on a difference between the cumulative storage values of the first and the second storage means when said light emitting device stops its light emission;

said storage means being capacitors having characteristics substantially the same as each other and said determining means including a comparing means which after said cumulative storage is suspended compares the charged amounts between the capacitors to determine the difference, said determining means further including a charging means for charging at a controlled rate the first capacitor with a charge proportional to the difference between the cumulative storage values detected by said comparing means, and counting means for indicating said charge input of said charging means, to determine the density or concentration of said gas or vapor on the basis of the indicated charge input.

7. An extinction type detector as claimed in claim 6, said detector being adapted to operate from a DC power source, in which said suspending means includes comparing means, said comparing means comparing a selected voltage of said power source and the cumulative charged voltage of the second capacitor and outputting a signal for said suspending of the light emission driving of the light emitting device by the emission driving means when said charged voltage reaches said selected voltage of the power source.

8. An extinction type detector which detects and determines a concentration or density of a gas or vapor in a space on the basis of an attenuation of light due to the gas or vapor present within the space, which detector comprises:

a light emitting device;

drive means for periodically and repeatedly driving the light emitting device for emitting light in a sequence of ON/OFF cycles; a first photodetector device which is disposed at a position where it can receive light from said light emitting device, a gas or vapor detecting space existing between said first photodetector device and said light emitting device;

a second and a third photodetector device which are each disposed at a position where they can receive light from said light emitting device, said light being received under the conditions that the gas or vapor does not intervene between said second and third photodetector devices and said light emitting device;

first storage means for cumulatively storing photooutputs from said first photodetector device; second storage means for cumulatively storing photo-outputs from said second photodetector device, said stored outputs being accumualted as storage values from a pluraltiy of said ON/OFF cycles of said light emitting device, the storage value in each said storage means increasing for each said cycle wherein the associated photodetector device receives light;

light emission control means for controlling the amount of light emission of the light emitting device on the basis of a photo-output from said third photodetector device so that the photo-outputs from said second and said third photodetector device may substantially be constant;

means for limiting the number of said cycles in said sequence of ON/OFF cycles;

a determining means which, after said sequence of ON/OFF cycles is complete, determines the concentration or density of the gas or vapor within said detecting space based on a difference between the cumulative storage values of the first and second storage means, said storage values representing said cumulative stored plurality of photo-outputs.

9. An extinction type detector as claimed in claim 8, in which said storage means are capacitors having characteristics substantially the same as each other and said determining means includes a comparing means which compares the charged amounts between the capacitors to determine the difference.

10. An extinction type detector which detects and determines a concentration or density of a gas or vapor in a space on the basis of an attenuation of light due to the gas or vapor present within the space, which detector comprises:

a light emitting device;

drive means for periodically driving the light emitting device for emitting light in a sequence of ON/OFF cycles; a first photodetector device which is disposed at a position where it can receive light from said light emitting device, a gas or vapor detecting space existing between said first photodetector device and said light emitting device;

a second and a third photodetector device which are each disposed at a position where they can receive light from said light emitting device, said light being received under the conditions that the gas or vapor does not intervene between said second and third photodetector devices and said light emitting device;

first storage means for cumulatively storing photooutputs from said first photodetector device;

second storage means for cumulatively storing photo-outputs from said second photodetector device, said stored outputs being accumualted from a plurality of said ON/OFF cycles of said light emitting device;

light emission control means for controlling the amount of light emission of the light emitting device on the basis of a photo-output from said third photodetector device so that the photo-outputs from said second and said third photodetector device may substantially be constant;

a determining means which determines the concentration or density of the gas or vapor within said detecting space based on a difference between the cumulative storage values of the first and second storage means, said storage values representing said cumulative stored plurality of photo-outputs;

said storage means being capacitors having characteristics substantially the same as each other and said determining means including a comparing means which compares the charged amounts between the capacitors to determine the difference, said determining means further including a charging means for charging the first capacitor on the basis of the difference between the cumulative storage values detected by said comparing means and a counting means for counting the charging time of said charging means, to determine the density or concentration on the basis of the charging time.

11. An extinction type detector as claimed in claim 10, in which the light emission control means is a differential amplifier having inputs of a driving voltage for said light emitting device by the driving means and photo-output voltage of the third photodetector device, and said amplifier outputs a signal for driving said light emitting device in inverse proportion to a difference between the photo-output and driving voltages.

* * * * *